(12) United States Patent  
Walter et al.

(10) Patent No.: US 7,597,846 B2  
(45) Date of Patent: Oct. 6, 2009

(54) APPARATUS FOR PRODUCING TISSUE ARRAYS

(75) Inventors: Roland Walter, Neulussheim (DE); Rolf Metzner, Dossenheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 449 days.

(21) Appl. No.: 11/469,048

(22) Filed: Aug. 31, 2006

(65) Prior Publication Data

US 2007/0059816 A1 Mar. 15, 2007

(30) Foreign Application Priority Data

Sep. 1, 2005 (DE) ........................ 10 2005 041 780  
Sep. 1, 2005 (DE) ........................ 10 2005 041 781  
Sep. 1, 2005 (DE) ........................ 10 2005 041 782

(51) Int. Cl.  
*G01N 21/00* (2006.01)  
*C12M 1/38* (2006.01)  
*G01N 31/00* (2006.01)  
*C12M 1/00* (2006.01)

(52) U.S. Cl. ........................ 422/63; 422/64; 422/65; 422/66; 422/67; 435/286.3; 435/307.1; 435/287.1

(58) Field of Classification Search ........................ None  
See application file for complete search history.

(56) References Cited

U.S. PATENT DOCUMENTS

| 6,103,518 | A  | 8/2000 | Leighton |
| 6,383,801 | B1 | 5/2002 | Leighton |
| 6,699,710 | B1 | 3/2004 | Kononen et al. |
| 2002/0106626 | A1 | 8/2002 | Muraca |
| 2003/0017446 | A1 | 1/2003 | Chasse et al. |

FOREIGN PATENT DOCUMENTS

WO  00/52132 A1  9/2000

*Primary Examiner*—Jill Warden  
*Assistant Examiner*—Neil Turk  
(74) *Attorney, Agent, or Firm*—Hodgson Russ LLP

(57) ABSTRACT

An apparatus for producing a tissue array, having at least one receiver block (1) and at least one donor block (2) that comprises tissue (3) to be investigated, is described. The donor block (2) comprises tissue (3) to be investigated, a first hollow needle (4) for creating a cavity in the receiver block (1), and a second hollow needle (5) for removing a sample from the tissue (3) and introducing the sample (3) into the cavity of the receiver block (1), being provided. For positioning of the first and/or the second hollow needle (4; 5) above the receiver block (1) and/or the donor block (2), a positioning array (11) having predefined markings, as well as a movably mounted lever, are provided for transferring the position of the markings onto a corresponding position on the donor block (2) and/or onto a corresponding position on the receiver block (1).

8 Claims, 2 Drawing Sheets

APPARATUS FOR PRODUCING TISSUE ARRAYS

CROSS REFERENCE TO RELATED APPLICATIONS

This application claims priority of German patent application no. 10 2005 041 781.7 filed Sep. 1, 2005, which is incorporated by reference herein. This application also claims priority of German patent application no. 10 2005 041 780.9 filed Sep. 1, 2005 and German patent application no. 10 2005 041 782.5 filed Sep. 1, 2005, both of which are incorporated by reference herein.

FIELD OF THE INVENTION

The invention concerns an apparatus and method for producing tissue arrays in a paraffin block, such that the block may be sectioned by a microtome to make a specimen slide having an array of tissue samples observable by microscope.

BACKGROUND OF THE INVENTION

Tissue arrays, also called tissue microarrays (TMAs), contain a plurality of different tissue samples in a single receiver block or paraffin block. The receiver block is sectioned in the usual manner with a microtome, and the section is applied onto a specimen slide. The specimen slide then contains a plurality of different tissue samples. Because of the large number of tissue samples on a single specimen slide, it is possible to stain or process all the samples under the same conditions. As a result, even very complex and expensive staining methods, for example those derived from immunohistochemistry (IHC) or in-site hybridization (ISH) for revealing DNA or RNA, can be applied effectively.

The production of tissue arrays is very time-consuming, however, since a plurality of different samples (up to 1,000) are arranged next to one another in one receiver block. From the various tissue or sample blocks, a tissue core is punched out with a hollow needle and transferred into a correspondingly prepared receiver block.

Before a tissue core is removed from a sample block, the corresponding site on the sample block must be located and marked. It has proven useful for this purpose, in practice, first to produce usual microtome sections from a sample block, apply them onto specimen slides, stain them using a standard method, and have them inspected by a pathologist. The pathologist then selects the sites of interest on the specimen slide, and marks that site directly on the specimen slide.

The laboratory worker producing the tissue arrays then has the task of locating, on the tissue block or donor block, the sites marked on the specimen slide, and removing a tissue core at the corresponding sites.

Punched-out portions or paraffin cores are also removed, using a hollow needle, from the receiver block, which as a rule is made of paraffin. The tissue cores are then introduced into the cavity thus created. As mentioned, as many as 1,000 tissue cores—depending on the application—can be arranged to form an array on one paraffin block. From these dimensions alone, it is apparent that the diameters of the tissue cores are less than 1 mm, and reliable and simple transfer of the tissue cores into the punched hole in the paraffin block is therefore possible only with special equipment.

An apparatus for producing a tissue array is known from U.S. Pat. No. 6,103,518. This apparatus is characterized in that the receiver block is arranged in stationary fashion, and possesses thereabove a pivotably mounted needle holder for two hollow needles. The needle holder is aligned onto the receiver block by way of an X-Y micrometer displacement device. The two needles—one for punching out the receiver block, the other for removing the tissue core—can be brought alternately into the working position.

For removal of the tissue core from the tissue block, the latter is placed manually, together with a U-shaped frame, above the paraffin block and aligned onto the hollow needle.

With this apparatus, it has proven difficult to locate, on the tissue block, the site marked on the specimen slide, and furthermore to ensure reliable introduction of the tissue core into the paraffin block.

An automated device for producing tissue arrays is known from U.S. Pat. No. 6,383,801 B1. Here both multiple paraffin blocks and multiple tissue blocks are arranged on an X-Y scanning stage. Also provided are two hollow needles operating independently of one another, of which one makes the punched holes in the paraffin block and the other is responsible for tissue core removal.

This device is very complex and moreover does not solve the problem of easily locating a marked site on the tissue block.

SUMMARY OF THE INVENTION

It is the object of the present invention to improve a manually operating apparatus for producing tissue arrays in such a way that simple and reliable positioning of the respective hollow needles above the respective blocks becomes possible.

This object is achieved, according to the present invention, by the features described in the present specification. Further advantageous developments of the invention are also described in the present specification.

The invention is characterized in that for positioning of the first and/or the second hollow needle, a positioning array having predefined markings, as well as a movable arm, are provided for transferring the position of the markings onto a corresponding position on the donor block and/or onto a corresponding position on the receiver block. The position of the marking on the positioning array is transferred via the movable arm to the respective needle or to the block, so that complex positioning is eliminated.

In a development of the invention, the movable arm is embodied rotatably and displaceably.

In a further embodiment of the invention, the movable arm is rotatably mounted and embodied as a pantograph.

In a development of the invention, the pantograph comprises two scissor arms joined to one another, so that a specific conversion ratio can be implemented by way of different dimensions of the scissor arms. Very accurate positioning of the hollow needles above the tissue block or paraffin block can thereby be achieved.

In a further embodiment of the invention, the first scissor arm comprises a receptacle for the first and/or the second hollow needle, and the second scissor arm comprises a receptacle for a detent pin.

In a development of the invention, the markings on the positioning array are embodied as detent holes. By exchanging the positioning array for a different array having more or fewer markings or detent holes, different tissue arrays can be produced without major modification.

In a development of the invention, the first and the second hollow needle are arranged next to one another on a needle holder, and the needle holder is embodied rotatably. The two different needles can thus be positioned successively above the receiver block, in order on the one hand to make the necessary punched hole in the receiver block and on the other hand to place the tissue core in the punched hole of the receiver block. The one end of the scissor arm carries a punching lever for actuation of the hollow needle.

In a further embodiment of the invention, multiple first and multiple second hollow needles, having different diameters, are arranged circularly next to one another on the needle holder, so that differently dimensioned tissue arrays are also producible. This also ensures that the diameter of the first hollow needle for punching out the receiving block or the paraffin block is larger than the diameter of the second hollow needle for removing the sample.

BRIEF DESCRIPTION OF THE DRAWINGS

The invention will be explained in more detail with reference to an exemplifying embodiment, with the aid of the schematic drawings in which.

DETAILED DESCRIPTION OF THE INVENTION

Figure 1:
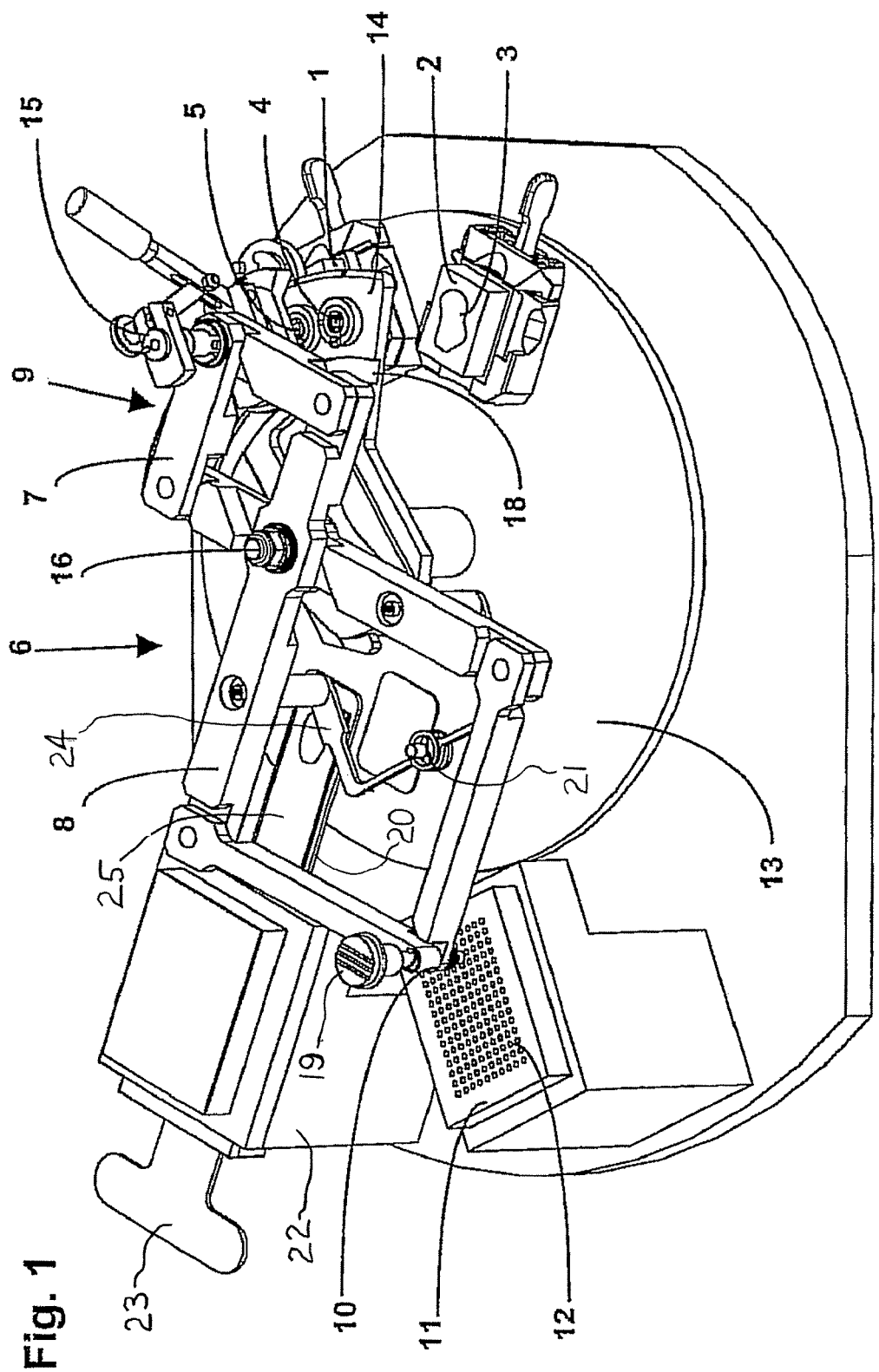
FIG. 1 is a view of the apparatus having the pantograph.

FIG. 1 is a view of the apparatus for producing a tissue array, having a receiver block 1 and a donor block 2 that contains tissue 3 to be investigated. Donor block 2 and receiver block 1 are arranged on a turntable 13. Also provided is a pivotably embodied needle holder 14 that carries a first hollow needle 4 and a second hollow needle 5. First hollow needle 4 serves to create a punched hole in receiver block 1, and second hollow needle 5 is provided in order to remove a tissue core from tissue 3.

The apparatus comprises a pantograph 6, mounted via a rotary shaft 16, having two scissor arms 7 and 8 joined to one another, the end of first scissor arm 7 carrying a receptacle 9 for a punching lever 15 for selectable actuation of first and second hollow needles 4; 5. The end of second scissor arm 8 is equipped with a detent pin 10 that has associated with it a positioning array 11 having individual detent holes 12. A positioning knob 19 is located atop detent pin 10.

The position of detent pin 10 on the positioning array is transferred via the rotatably mounted pantograph to receptacle 9 for punching lever 15. Needle holder 14 is joined in positively engaged fashion (FIG. 2) to first scissor arm 7, and thereby follows the movement of punching lever 15. Selection of the corresponding hollow needle is accomplished by a pivoting motion of needle holder 14 about rotary shaft 16. For punching, receiver block 1 is positioned via turntable 13 below the corresponding first hollow needle 4; first hollow needle 4 is then driven by punching lever 15 into receiver block 1 and makes a punched hole therein. Removal of a tissue core from donor block 2, and introduction of the tissue core into the punched hole in receiver block 1, are accomplished analogously. Pantograph 6 and positioning array 11 ensure that the positions of first and second hollow needle 4; 5 are precisely maintained.

It is of course within the scope of the invention to immobilize the respective positions of the turntable by way of additional detents in order to ensure simple and rapid operation, or also to arrange multiple donor blocks and/or receiver blocks simultaneously.

Figure 2:
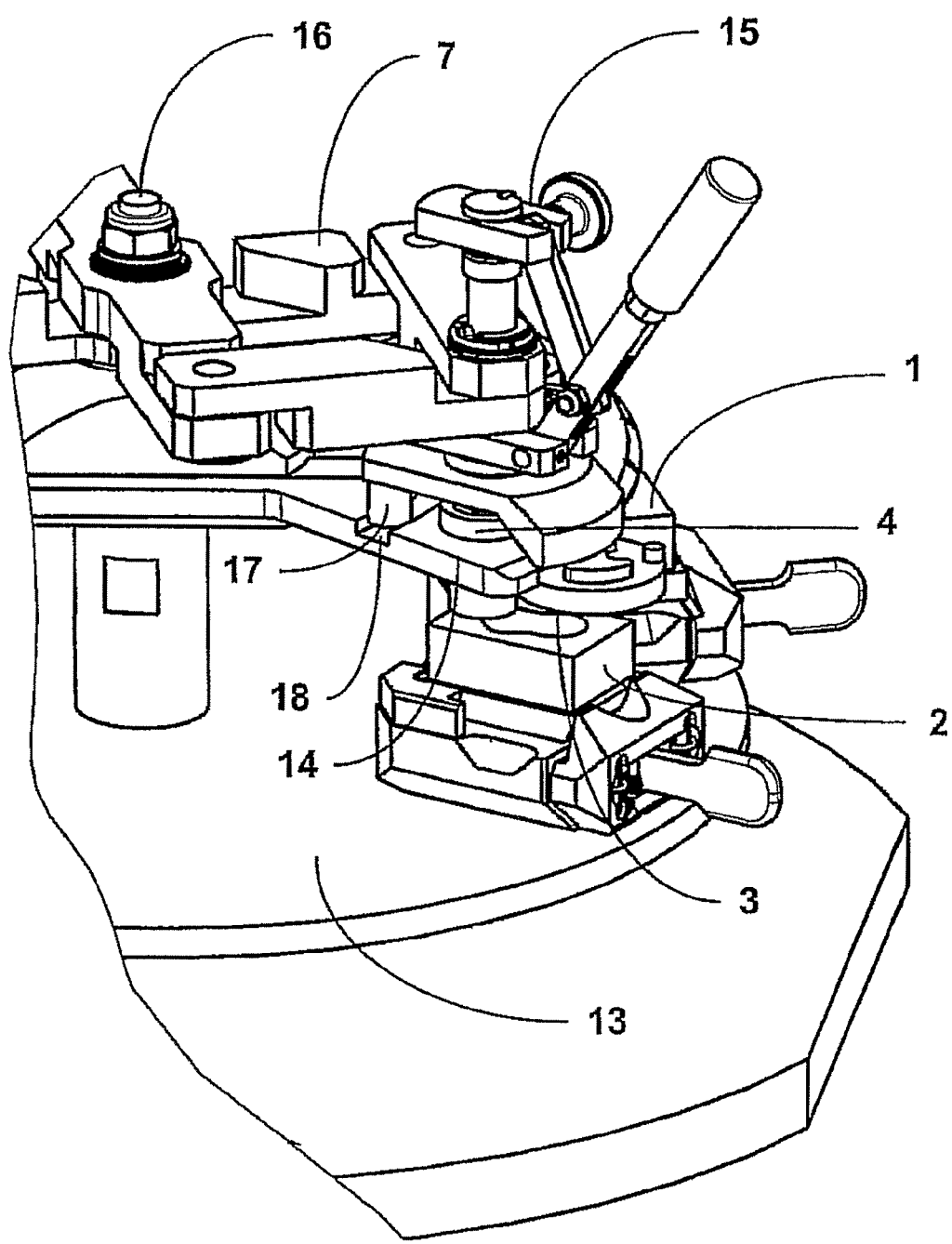
FIG. 2 is a detail view of the apparatus having a needle holder.

FIG. 2 is a detail view of needle holder 14, which is mounted rotatably and displaceably about rotary shaft 16. Needle holder 14 comprises a groove 18 into which a cam 17 positively engages. Cam 17 is joined to first scissor arm 7. A movement of scissor arm 7 is transferred via cam 17 and groove 18 to needle holder 14.

Precise removal of a tissue core is now described. A fixedly arranged slider receptacle 22 for a specimen slide holder 20 is provided. Specimen slide holder 20 is arranged movably via a slider 23 in slider receptacle 22, and carries a marked specimen slide 25. Present on specimen slide 25 is a microtome section of donor block 2 having tissue 3.

Donor block 2 is arranged below specimen slide holder 20. By way of the movably mounted specimen slide holder 20, congruency is created between the microtome section and tissue 3 in donor block 2.

A sighting device 21 is arranged on second scissor arm 8 via a sight holder 24. Sighting device 21 is aligned onto the marked site on specimen slide 25 via positioning knob 19. This movement is transferred via pantograph 6 to punching lever 15 and needle holder 14.

Removal of a tissue core from donor block 2 is then performed by the fact that donor block 2 is rotated via turntable 13 out of its position beneath sighting device 21 into a position beneath needle holder 14, and second hollow needle 5 is moved via punching lever 15 into tissue 3 in order to remove a tissue core. Pantograph 6 and sighting device 12 ensure that tissue 3 is removed from the site being sighted onto.

PARTS LIST

1 Receiver block, paraffin block
2 Donor block, tissue block
3 Tissue
4 First hollow needle
5 Second hollow needle
6 Pantograph
7 First scissor arm
8 Second scissor arm
9 Receptacle for 4; 5
10 Detent pin
11 Positioning array
12 Detent holes
13 Turntable
14 Needle holder
15 Punching lever
16 Rotary shaft
17 Cam
18 Groove in 14
19 Positioning knob
20 Specimen slide holder
21 Sighting device
22 Slider receptacle
23 Slider
24 Sight holder
25 Specimen slide

What is claimed is:

1. An apparatus for producing a tissue array comprising:
a receiver block;
a donor block including tissue to be investigated;
a first hollow needle for creating a cavity in the receiver block;
a second hollow needle for removing a sample of tissue from the donor block and introducing the sample into the cavity in the receiver block;
a positioning array having predefined markings; and
a pantograph including a first scissor arm and a second scissor arm joined to one another, the first scissor arm being mechanically connected to the first and second needles and the second scissor arm being mechanically connected to the positioning array, wherein the pantograph positions the first and second hollow needles with respect to the receiver block and the donor block and transfers a position of a selected one of the markings of the positioning array onto a corresponding position on either of the receiver block and the donor block.

2. The apparatus for producing a tissue array according to claim 1, wherein the first scissor arm includes a receptacle for receiving either of the first hollow needle and the second hollow needle, and the second scissor arm includes a detent pin.

3. The apparatus for producing a tissue array according to claim 1, wherein the markings on the positioning array are embodied as detent holes.

4. The apparatus for producing a tissue array according to claim 2, wherein the markings on the positioning array are embodied as detent holes sized to receive the detent pin.

5. The apparatus for producing a tissue array according to claim 1, further comprising a turntable, wherein the receiver block is arranged on the turntable.

6. The apparatus for producing a tissue array according to claim 2, further comprising:
   a needle holder associated with receptacle, wherein the first hollow needle and the second hollow needle are arranged next to one another on the needle holder, and the needle holder is movable relative to the receptacle to align a selected one of the first hollow needle and the second hollow needle with the receptacle; and
   a punching lever aligned with the receptacle for actuating a hollow needle aligned with the receptacle.

7. The apparatus for producing a tissue array according to claim 5, wherein the donor block is arranged on the turntable.

8. The apparatus for producing a tissue array according to claim 6, wherein a plurality of first hollow needles and a plurality of second hollow needles, having different diameters, are arranged next to one another in a circular arc on the needle holder.

* * * * *